United States Patent
Prutchi et al.

[11] Patent Number: 5,978,710
[45] Date of Patent: Nov. 2, 1999

[54] IMPLANTABLE CARDIAC STIMULATOR WITH SAFE NOISE MODE

[75] Inventors: David Prutchi; Patrick J. Paul, both of Lake Jackson, Tex.

[73] Assignee: Sulzer Intermedics Inc., Angleton, Tex.

[21] Appl. No.: 09/012,854

[22] Filed: Jan. 23, 1998

[51] Int. Cl.[6] .................................................. A61N 1/365
[52] U.S. Cl. ............................... 607/17; 607/9; 607/63; 607/2; 600/513; 600/547
[58] Field of Search ................................ 607/4, 5, 6, 8, 607/9, 14, 17, 18–20, 24, 28, 63, 27, 2; 600/547, 506, 513

[56] References Cited

U.S. PATENT DOCUMENTS

| | | | |
|---|---|---|---|
| 4,091,818 | 5/1978 | Brownlee et al. | 607/9 |
| 4,516,579 | 5/1985 | Irnich | 128/419 |
| 4,733,667 | 3/1988 | Olive et al. | 607/24 |
| 4,940,052 | 7/1990 | Mann et al. | 607/19 |
| 5,010,887 | 4/1991 | Thornander | 128/696 |
| 5,031,614 | 7/1991 | Alt | 607/19 |
| 5,144,949 | 9/1992 | Olson | 607/17 |
| 5,269,299 | 12/1993 | Duncan | 607/9 |
| 5,314,453 | 5/1994 | Jeutter | 607/61 |
| 5,531,772 | 7/1996 | Prutchi | 607/17 |
| 5,697,958 | 12/1997 | Prutchi . | |
| 5,817,136 | 10/1998 | Nappholz et al. | 607/17 |

OTHER PUBLICATIONS

George H. Crossley, Lisa A. Kiger, Wesley K. Haisty, Tony W. Simmons, Matt Zmijewski and David M. Fitzgerald; False–Positive Behavior with the dP/dt Sensing Pacemaker: A Rare Complication of Physiological Sensor, pp. 2492–2495; North Carolina and Minneapolis, Minnesota.

*Primary Examiner*—William E. Kamm
*Assistant Examiner*—Kennedy J. Schaetzle
*Attorney, Agent, or Firm*—Schwegman, Lundberg, Woessner & Kluth, P.A.

[57] ABSTRACT

An implantable medical device for electrically stimulating the heart to beat generally includes a processor, a plurality of electrodes, a sense amplifier, a pulse generator, and a heart status monitor. The processor can determine when the patient has entered an environment of high electromagnetic interference. When this occurs, the processor forces the implantable device into a safe noise mode. While in the same noise mode (which preferably continues while the patient is experiencing the electromagnetic interference), the implantable device paces the heart on demand and inhibits pacing during the vulnerable period. The processor determines when the vulnerable period is occurring and when the heart needs to be paced by monitoring a status signal from the heart status monitor. The status signal generated by the heart status monitor preferably is not sensitive to the electromagnetic interference, and thus the processor can determine the bio-mechanical state of the heart during a cardiac cycle even in the face of high electromagnetic interference. The heart status monitor preferably includes an impedance measurement circuit, but may include any type of cardiac sensor that can generate a status signal from which the processor can determine the beginning and ending of the vulnerable period. Accordingly, even during a period of high electromagnetic interference, the implantable device can provide on demand pacing support to the patient.

16 Claims, 5 Drawing Sheets

IMPLANTABLE CARDIAC STIMULATOR WITH SAFE NOISE MODE

BACKGROUND OF THE INVENTION

1. Field of the Invention

The present invention relates generally to cardiac stimulating devices. More particularly, the present invention relates to an implantable cardiac pacemaker or cardioverterdefibrillator with a safe mode of operation during the occurrence of externally generated noise or interference.

2. Description of the Related Art

Figure 1:
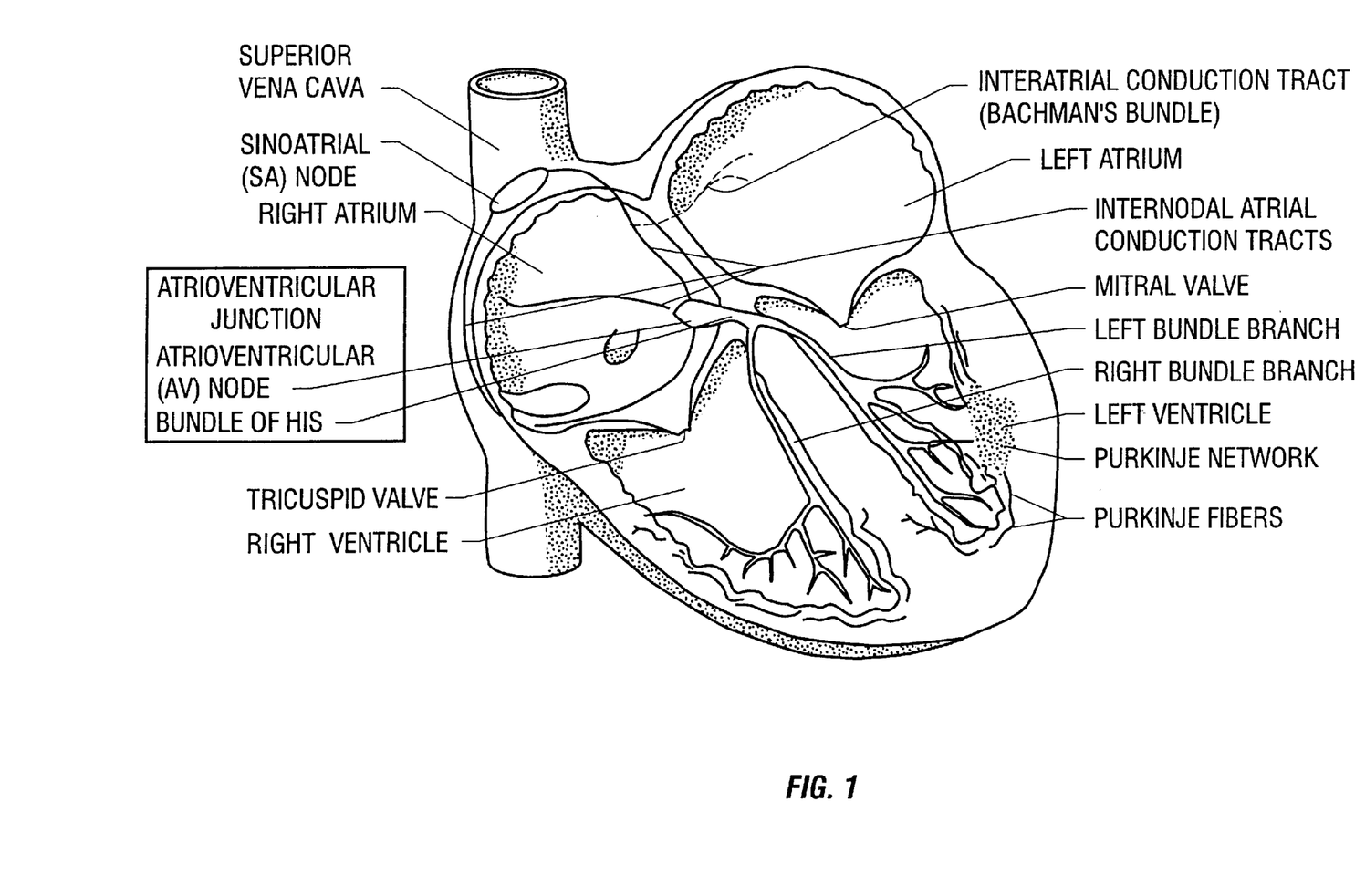
FIG. 1 is a schematic cut-away view of a human heart, in which the various relevant parts are labeled.

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Certain other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer" as it is commonly described) is a medical device which includes an electronics assembly and one or more leads connecting the electronics assembly to the heart. Electrodes on the distal end of the leads include an exposed conducting surface adjacent to or in contact with the heart tissue. The pacemaker delivers electrical pulses via the electrodes to the patient's heart in order to stimulate the heart to contract and beat at a desired rate.

Pacemakers originally were designed to operate asynchronously. That meant the pacemaker emitted an electrical pulse that was delivered to the heart through the pacemaker's electrodes at a constant rate. Asynchronous pacemakers paced the heart at a constant, preselected rate generally thought to be sufficient for the particular patient (e.g., 70 pulses per minute). This type of pacing protocol, however, unnecessarily expended the energy of the pacemaker's battery (which has a limited life) because the hearts of many patients were capable of beating on their own, at least occasionally, without the need for an artificially generated pacemaker pacing pulse. Thus, an asynchronous pacemaker may expend energy pacing the heart at a time when the heart's natural pacemaker and conduction system are functioning properly and not in need of artificial stimuli.

Pacemakers today typically are provided with the capability to determine whether the heart is able to beat on its own, and if so, the pacemaker will not pace the heart. If, however, the heart cannot beat on its own, the modern pacemaker will pace the heart instead. This type of pacemaker is referred to as a "demand" pacemaker because pacing pulses are generated by the pacemaker only as needed by the heart (i.e., on "demand").

Some patients have disease processes that may cause an "arrhythmia," which is an abnormal cardiac rhythm. For some of these patients the arrythmias may be characterized by an excessively slow heart rate (termed "bradycardia") or an excessively fast and irregular heart rate (termed "tachyarrhythmia"). Tachyarrhythmia may degenerate into fibrillation in which the affected cardiac chamber merely quivers and loses all of its blood pumping capability. If the fibrillation condition occurs in a ventricular chamber of the heart (a condition commonly called "ventricular fibrillation"), the patient will normally die within minutes. In patients undergoing pacing therapy, a tachyarrhythmia hopefully can be terminated with an antitachyarrhythmia pacing protocol which generally includes a fast pacing rate to interfere with the focus of the arrhythmia. If antitachyarrhythmia pacing does not stop the arrhythmia, a defibrillation pulse is necessary to terminate the arrhythmia.

Patients that are susceptible to tachyarrhythmias are candidates for an implantable cardioverterdefibrillator ("ICD") which is a device that senses the onset of tachyarrhythmias and generates antitachyarrhythmia pacing pulses and, if needed, a subsequent defibrillation pulse to terminate the arrhythmia. Patients that require an ICD also generally require pacing support such as that provided by pacemakers. Thus, in addition to a defibrillation capability, an ICD typically also includes a pacing capability to pace the heart on demand.

Figure 2:
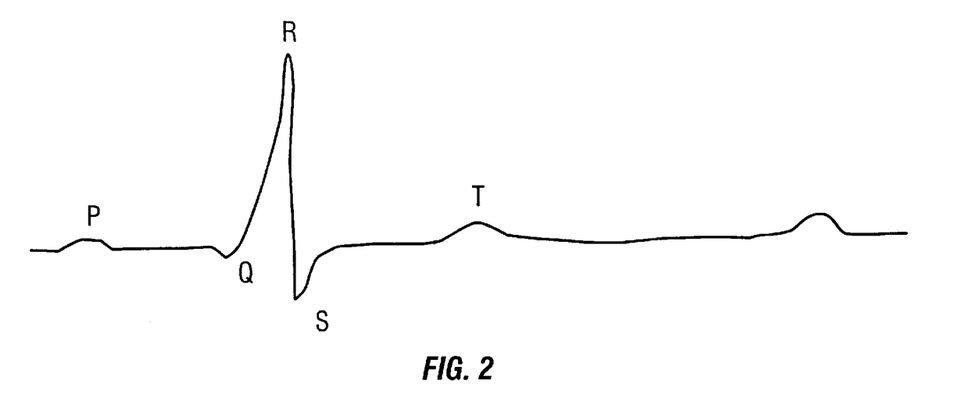
FIG. 2 is a portion of an exemplary surface electrocardiogram.

In some patients with pacemakers/ICD's observed that the pacemaker/ICD itself has demonstrated the propensity to induce a tachyarrhythmia which may degenerate into a fatal fibrillation. The reason for this phenomenon can be described with respect to FIG. 2 in which a ventricular repolarization wave (during which the ventricle relaxes after contracting) is detected by the surface electrocardiogram ("ECG") as the so-called "T-wave". The T-wave occurs approximately 150–400 milliseconds after the occurrence of the ventricular depolarization wave shown on the surface ECG as the QRS complex. Around the time the T-wave is detected, various portions of the ventricles are undergoing repolarization, and as such are not sensitive to stimulation.

This period of time in which cardiac tissue is not sensitive to electrical stimulation is called the refractory period.

If pacing occurs during the refractory period, a slowly propagating action potential initiated by tissue which is sensitive to stimulation may cause the stimulation of tissue which was not viable for stimulation at the time the original stimulus was generated. This propagating wave may later reach the tissue which was originally stimulated at a time when it has already repolarized, and thus cause its depolarization anew. If this sequence of events occurs, a reentrant loop is created which causes the ventricle to beat at a rate determined by the period of the reentrant loop. This sequence causes what is known as a "reentrant tachycardia," and may degenerate into fibrillation. The period of time during which a pacing pulse may cause tachycardia is referred to as the "vulnerable period," and an ICD should avoid pacing the heart during the vulnerable period. The implanted device determines the vulnerable period by monitoring the electrical activity of the heart.

A conventional pacemaker or ICD generally includes a sense circuit for monitoring the electrical activity of the heart. The sense circuit usually includes a highly sensitive amplifier. The electrodes and leads of the implanted device may act as antennae and pick up electromagnetic signals that have non-cardiac sources, including even signals generated from a source external to the body. Such sources of external signals generally are referred to as "electromagnetic interference" ("EMI"). Sources of EMI include metal detectors such as are used in airports, welders, radio transmitters, microwave ovens, etc. The electrical signals conducted to the implanted device from the electrodes implanted in the heart may thus include EMI superimposed on the heart's natural cardiac signal. The EMI component of the signal represents noise and preferably is ignored.

Although the implanted device usually has some filtering circuits for attenuating noise superimposed on a cardiac signal, in some situations the noise component may be such that the device's filters cannot adequately eliminate the noise. If a patient with an ICD walks through a metal detector, for example, the resulting EMI signal may overwhelm the cardiac signal picked up by the electrodes. Although the implanted device may be able to determine that it is receiving an excessive amount of noise, the device may be unable to extract the true cardiac signal from the noise. Because the true cardiac electrical signal cannot be accurately ascertained, the implanted device can not determine when the vulnerable period of each cardiac cycle is occurring. Such devices are thus often supplied with a "noise mode" of operation in which the device attempts to respond to the noise in some appropriate manner.

Up to now, pacemaker and ICD designers have been faced with a dilemma. If the implantable device is in a high noise field and the device discontinues pacing to avoid pacing during the vulnerable period, the patient may suffer severe harm or death if the patient indeed needed pacing support. On the other hand, if the device does provide pacing during a high noise event, the pacing will have to be performed asynchronously (fixed rate) rather than on demand because the noise disrupts the device's sensing ability to determine when the patient needs a pacing pulse. However, if the pacemaker or ICD provides asynchronous pacing support because the patient may need it, a pacing pulse may occur during the vulnerable period and the patient's heart may fibrillate with serious or lethal consequences. This dilemma generally has been resolved in favor of continued pacing, although asynchronously, because the probability is greater that the patient will need pacing than the patient will enter into ventricular fibrillation as a result receiving a pacing pulse during the vulnerable period. Accordingly, the appropriate noise mode generally includes asynchronous pacing with no sensing capability. When the pacemaker or ICD enters the noise mode, the sense circuit is disabled, or ignored, and the device paces at a constant rate without regard to whether the heart is able to beat on its own.

Although this may be an appropriate response to noise for some patients, asynchronous pacing without sensing may cause harm to other patients. This latter group of patients includes patients for which a tachyarrhythmia may be induced by a pacing pulse that occurs during the vulnerable period of the cardiac cycle. For this group of patients, an asynchronous pacing mode of operation may result in the implantable device emitting a pacing pulse during the vulnerable period. If this were to happen, not only may the pacing pulse cause a tachyarrhythmia, but the arrhythmia may degenerate into a fatal fibrillation. However, because the sensing capability of the pacemaker or ICD is disabled during the noise mode in conventional devices, the device is not able to determine that the heart is experiencing the arrhythmia, and thus the device can respond with an appropriate antitachyarrhythmia pacing protocol or, if necessary, a defibrillation pulse. Thus, the classic asynchronous pacing noise mode may induce a fatal tachyarrhythmia and fibrillation in the patient at a time when the patient cannot be rescued by the delivery of a defibrillation shock. Although the probability of causing harm to a patient by pacing asynchronously during a high noise event is generally considered small, the possibility of harm nevertheless does exist and should be addressed.

Thus, there is a need for an implantable pacemaker or ICD to respond to the presence of noise in a more appropriate manner than current devices. The new device should not put the patient at risk from suffering a dangerous or fatal arrhythmia that is induced by the implanted device itself. The device preferably will able to determine the vulnerable period of each cardiac cycle during a high noise event and avoid pacing the heart during that period of time.

SUMMARY OF THE INVENTION

Accordingly, there is herein provided an implantable medical device, such as a pacemaker or implantable cardioverter/defibrillator, that electrically stimulates the heart to beat. The medical device generally includes a processor, a plurality of electrodes, a sense amplifier, a pulse generator, and a heart status monitor. The processor can determine when the patient has entered an environment of high electromagnetic interference. If, and when, the processor makes this determination, the processor forces the implantable device into a safe noise mode of operation. While in the safe noise mode (which preferably continues as long as the patient is in the presence of the electromagnetic interference), the implantable device paces the heart on demand. The processor determines when the heart needs to be paced by monitoring a status signal from the heart status monitor. The status signal generated by the heart status monitor is indicative of the physical or bio-mechanical state of the heart during a cardiac cycle and preferably is not sensitive to the electromagnetic interference. Using the status signal, the processor can determine the bio-mechanical state of the heart during a cardiac cycle and thus the vulnerable period, even in the face of high electromagnetic interference. Accordingly, the implantable device will pace the heart while experiencing a large EMI event but inhibit pacing during the vulnerable period.

The status signal generated by the heart status monitor is indicative of some aspect of the cardiac cycle. In accordance with the preferred embodiment, the heart status monitor includes a circuit used by the processor to determine the impedance between electrodes implanted in the heart or elsewhere in the patient's body. The status signal is thus indicative of the heart's impedance which varies in a periodic manner with each cardiac cycle. From the status signal, the processor determines the heart's impedance as a function of time during a cardiac cycle. From that determination, the processor can ascertain when the vulnerable period occurs and inhibit pacing during the vulnerable period.

Rather than determining the heart's impedance, the heart status monitor alternatively may include a cardiac sensor that can be used to provide the status signal to the processor. The sensor may be any one of a variety of sensors that can track a cardiac parameter that varies according to a pattern from one cardiac cycle to another. Accordingly, the sensor may include a pressure transducer for providing an indication of pressure inside one of the chambers of the heart. Further still, the sensor may include a volume transducer or flow transducer or any other sensor type that can generate a status signal from which the processor can determine the beginning and ending of the vulnerable period.

BRIEF DESCRIPTION OF THE DRAWINGS

Other objects and advantages of the invention will become apparent upon reading the following detailed description and upon reference to the accompanying drawings, wherein.

DETAILED DESCRIPTION OF THE PREFERRED EMBODIMENTS

Figure 3:
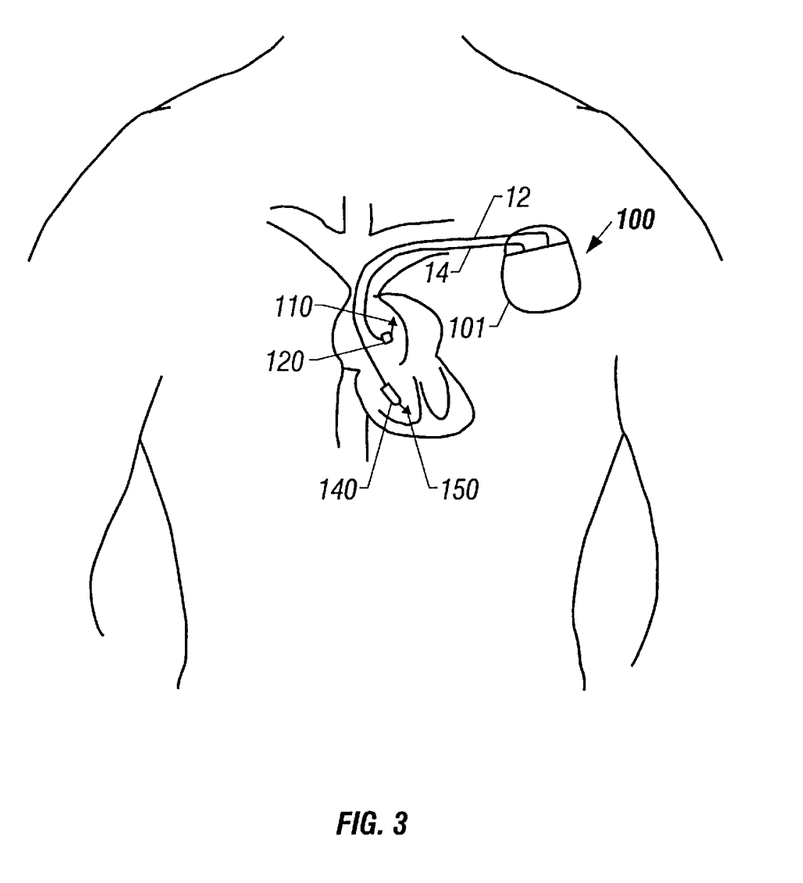
FIG. 3 is a schematic diagram of an implantable cardioverterdefibrillator constructed in accordance with the present invention and implanted in a human body.

Referring now to FIG. 3, an implantable medical device 100 constructed in accordance with the preferred embodiment is shown implanted and coupled, in an exemplary configuration, to the patient's heart by leads 12, 14. The implantable medical device 100 may include a pacemaker, combination cardioverterdefibrillator and pacemaker, or any other device that provides pacing support for the patient's heart. For purposes of describing the preferred embodiments of the invention, however, the implantable medical device 100 will hereafter be described as an implantable cardioverterdefibrillator ("ICD") with the understanding that pacemaker functions are also included. However, it should be understood that the invention may be employed in any of a variety of implantable medical devices, including simple pacemakers.

The arrangement shown in FIG. 3 represents a dual chamber pacing configuration in which two leads 12 and 14 are coupled to a housing or "can" 101 of the ICD. In the configuration shown, the leads are positioned in two chambers of the heart, lead 12 implanted in the right ventricle and the other lead 14 implanted in the right atrium. Each lead may incorporate any desired number of electrodes. The leads 12,14 shown in FIG. 3, for example, are bipolar leads meaning each lead includes two electrodes. Lead 14 includes a tip cathode electrode 110 and a ring anode electrode 120. Lead 12 includes a tip cathode electrode 150 and a shock coil 140 for delivering a defibrillation shock pulse. Some ICD leads include tip and ring electrodes as well as a shock coil. As one skilled in the art will understand, two, three, and four lead devices that have been used or suggested as various pacemaker or ICD configuration schemes in other applications may be employed in the present invention. Further, the ICD housing 101 itself can be used as an electrode. The configuration shown in FIG. 3 is intended to be exemplary only of the many lead configurations possible for ICD 100.

ICD 100 may also communicate with an external programmer (not specifically shown). If it is desired for the ICD 100 to include a communication capability, any one of a number of communication techniques may be used. Preferably, however, the communication technique used involves wireless transmission of control and data signals such as that disclosed by U.S. Pat. No. 5,314,453, incorporated here in by reference.

Figure 4A:
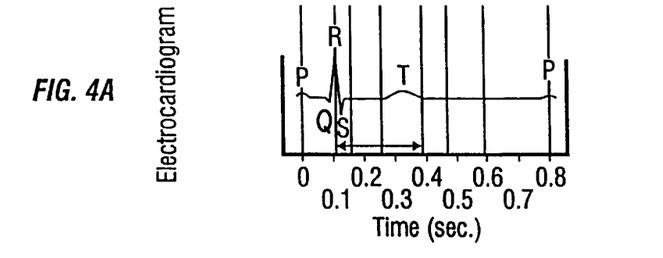
FIGS. 4A–4G show waveforms representing various cardiac parameters that vary with each cardiac cycle.
Figure 4B:
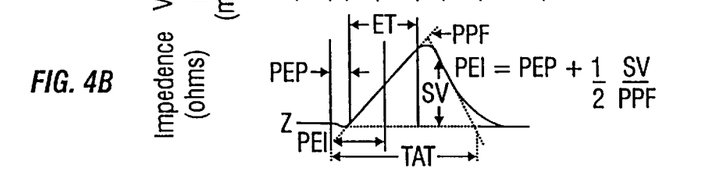
Figures 4C, 4D, 4E:
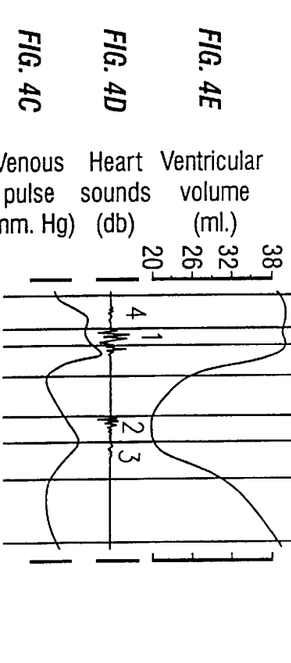
Figures 4F, 4G:
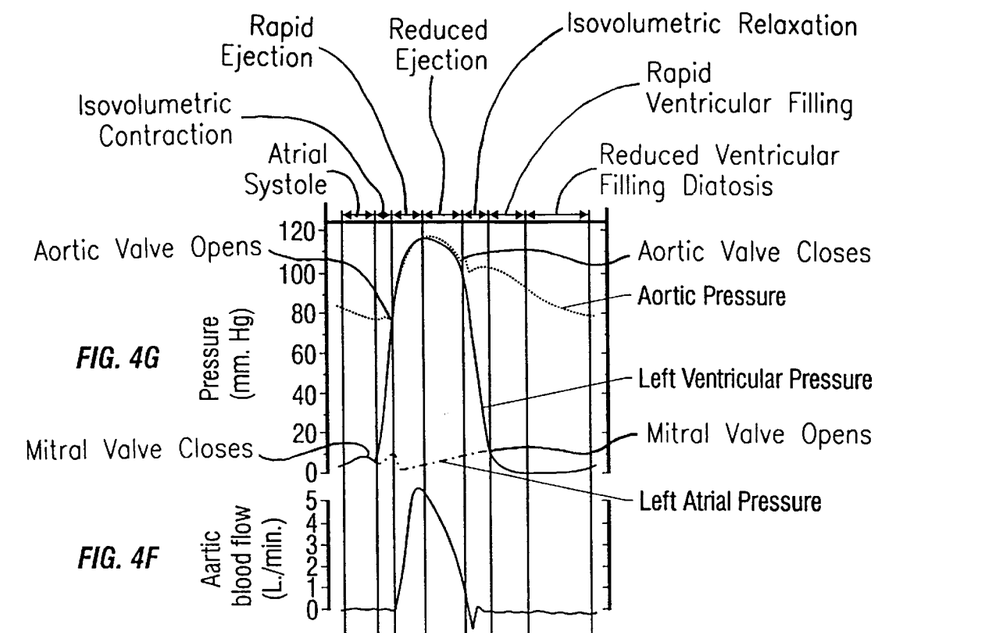

FIGS. 4A–4G illustrate that the bio-mechanical action of the ventricles begins to take place more or less at the same time that the electrical repolarization of the ventricles is occurring. FIG. 4A includes the surface ECG as in FIG. 2. Ventricular repolarization occurs approximately at the time of the T-wave on the surface ECG. FIGS. 4B–4G illustrate several time-varying parameters each one indicative of some aspect of the heart during a cardiac cycle. The variation of these parameters is illustrated generally over one cardiac cycle and the figures are aligned in time with the surface ECG of FIG. 4A. FIG. 4B shows the electrical impedance of the heart measured between a pair of the pacer's electrodes 110, 120, 140, 150. FIGS. 4C and 4D illustrate the venous pulse and heart sounds, respectively. The heart sounds are acoustic signals that are indicated as a type of resonant phenomena of cardiac structures and blood as a consequence of one or more sudden events in the heart (such as closure of a valve). FIG. 4E is the volume of the ventricle. The blood flow through the aorta is shown in FIG. 4F and the pressure of the left ventricle is shown in FIG. 4G. The waveforms of FIGS. 4B–4G are cyclical or periodic meaning they repeat with each cycle of the patient's heart. Thus, each of the parameters in FIGS. 4B–4G can be correlated to the cardiac cycle. Accordingly, by monitoring any one of these physical and electrical parameters, the ICD 100 can determine the current state of the heart and moreover, determine or estimate the beginning and ending of the vulnerable period. As previously mentioned, the vulnerable period is a period in which a pacing pulse may itself cause life-threatening fibrillation.

Figure 5:
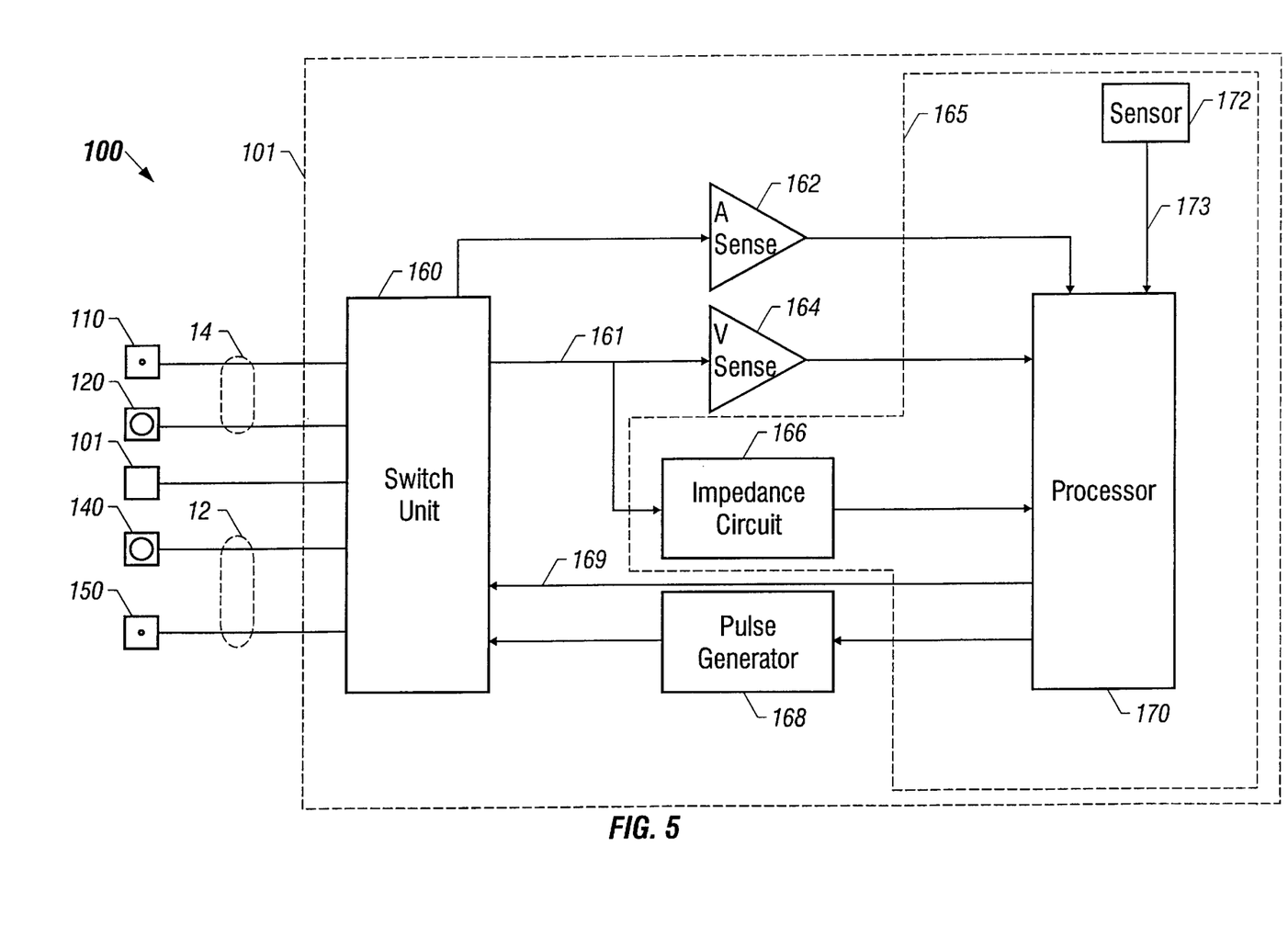
FIG. 5 is an exemplary block diagram of a preferred embodiment of the invention as may be employed in the cardioverterdefibrillator shown in FIG. 3.

The preferred embodiment of the ICD 100 is illustrated in the exemplary block diagram of FIG. 5. The ICD 100 generally includes a switch unit 160, atrial and ventricular sense circuits 162, 164, a heart status monitor 165 which includes a processor 170 and an impedance circuit 166 andor a sensor 172, and a pulse generator 168. The exemplary embodiment of FIG. 5 shows ICD 100 with five electrodes, namely atrial tip and ring electrodes 110 and 120, ventricular shock coil and tip electrodes 140, 150, and can electrode 101. The invention, however, may be practiced using any number of electrodes implanted in any chamber of the heart.

Referring still to FIG. 5, the atrial sense circuit 162 processes signals received from the atrial chamber of the heart via the atrial electrodes 110, 120 and the ventricular sense circuit 164 processes signals from the ventricular chamber via the ventricular electrodes 140, 150. The atrial and ventricular sense circuits 162, 164 generally include a low power, highly sensitive amplifier, a band pass filter, and a threshold detector (not specifically shown). The amplifier amplifies the electrical signal from the associated electrodes, and the band pass filter attenuates signals whose frequencies are outside the range of frequencies known to correspond to cardiac signals. The threshold detector compares the amplified and filtered signal to a reference signal to determine when a cardiac event (also referred to as a "sense event") has occurred. If the magnitude of the amplified and filtered cardiac signal exceeds the reference signal, the processor 170 determines that a sense event has occurred. The processor 170 may then pace the heart based either on detecting or not detecting sense events. For example, the processor 170 may initiate a ventricular pacing pulse if an atrial sense event has not been detected within a predetermined period of time following a previous atrial sense event.

The pulse generator 168 is employed to produce an appropriate electrical pulse to stimulate the desired chamber of the heart to beat. The processor 170 initiates the pulse generator 168 to produce a pacing pulse, and the pulse generator responds by delivering the pacing pulse to the desired chamber of the heart. The pulse generator may include a rate limiter to prevent the processor 170 from erroneously pacing the heart at an excessively high rate.

Switch unit 160 preferably includes multiple solid state switches (not specifically shown) and preferably one switch connects to each electrode. The states of the switches are controlled by processor 170 via control lines 169. The processor 170 controls the state of switch unit 160 to connect the electrodes to either the sense circuits 162, 164 or the pulse generator 168. Further, the processor 170 may control the state of each switch contained within switch unit 160 independently of other switches that may be contained within switch unit 160. The processor 170 connects the desired electrodes (either the atrial electrodes 110, 120 or the ventricular electrodes 140, 150) to pulse generator 168 when the processor desires to initiate a pacing pulse to the appropriate atrial or ventricular chamber. The processor 170 may also be employed to sense the electrical activity in either the atrial or ventricular chambers, or both, by altering the state of switch unit 160 to connect the desired electrodes to the corresponding sense circuit 162, 164.

The ICD 100 preferably operates in a predetermined pacing mode that is suitable for the patient. Accordingly, ICD 100 may be programmed to operate in one of a number of pacing modes. For example, the ICD 100 may be programmed to sense electrical activity in the atrium, and then to pace the ventricle following a predetermined time delay after the atrial sense event if the ventricle has not beat on its own.

The ICD 100 can determine when it is in a high noise environment such as may occur when the patient is near a source of EMI. As previously mentioned, this high noise condition may occur as the patient walks through a metal detector or is near a radio transmitter, welder, security surveillance system, etc. The EMI from such a source mixes in with and thus distorts, the naturally occurring cardiac signal being monitored by the processor 170 by one or both of the sense circuits 162,164. The processor 170 can determine when the pacer 100 is experiencing excessive EMI using any one of a number and of processing techniques such as that described in U.S. Pat. Nos. 5,010,887, 4,516,579 and 5,697,958, incorporated herein by reference.

Referring still to FIG. 5, if the processor 170 determines that the ICD 100 is in a high noise environment, the processor 170 preferably changes the mode of operation to a safe noise mode. In the safe noise mode of the preferred embodiment, all intracardiac electrogram sensing activity is terminated, and the electrogram sense circuits 162, 164 are turned off by switch unit 160 and the processor 170. Alternatively, processor 170 may be programmed to ignore the output signals of sense circuits 162, 164 during the period that high EMI is detected. As used herein, the term or phrase "discontinues monitoring" as applied to the processor includes either way to terminate electrogram sensing. Rather than switching to an asynchronous pacing mode during periods that high EMI is present, as do prior art implantable devices, ICD 100 instead switches to an inhibited, safe noise pacing mode. In the preferred safe noise pacing mode, the processor 170 continues to pace the heart if the heart needs to be paced (i.e., on demand). However, rather than monitoring the electrical activity of the heart via the sense circuits 162, 164, the processor 170 determines the biomechanical state of the heart during the cardiac cycles using an alternative technique described below.

The alternative heart monitoring technique uses a heart status monitor 165 to determine the bio-mechanical state of the heart. According to the preferred embodiment, the heart status monitor includes impedance circuit 166. The impedance circuit 166 generally processes the electrical signal from a ventricular electrode and provides an output status signal to the processor 170. The processor 170 uses the status signal from the impedance circuit 166 to compute the impedance of the heart. As shown in FIG. 4B, the impedance of the heart varies in a rhythmic manner with each cardiac cycle. The impedance waveform of FIG. 4B reaches a peak shortly after the T-wave of the surface ECG. The processor 170 can determine when the heart is in the vulnerable period of the cardiac cycle by computing and tracking the heart's impedance. The impedance circuit 166 can be any suitable circuit, such as that described in U.S. Pat. No. 5,531,772, incorporated herein by reference. The impedance measurement technique described in U.S. Pat. No. 5,531,772is particularly beneficial because it is not very sensitive to EMI or other sources of noise.

Alternatively or additionally, the heart status monitor may include a sensor 172 to provide an indication of the bio-mechanical activity of the heart. Sensor 172, for example, may be a pressure transducer, a flow transducer, an accelerometer, a sound transducer, or any other type of device or combination of devices that provides a status signal via line 173 from which the processor 170 can determine the current state of the heart during each cardiac cycle. The sensor 172 should be one that is not susceptible to EMI. For example, the sensor 172 may comprise a pressure transducer that is incorporated into the distal end of one or both of the leads 12, 14 (i.e., the end implanted in the heart itself). Such a pressure transducer can provide an electrical signal to the processor 170 from which the processor can compute the atrial or ventricular pressure (as exemplified in FIG. 4G). If sensor 172 comprises a flow transducer or a volume transducer, the processor 170 can compute aortic blood flow as in FIG. 4F or ventricular volume as in FIG. 4E, respectively. In general, the ICD 100 may include any sensor from which the bio-mechanical state of the heart can be determined during a high noise event.

Figure 6:
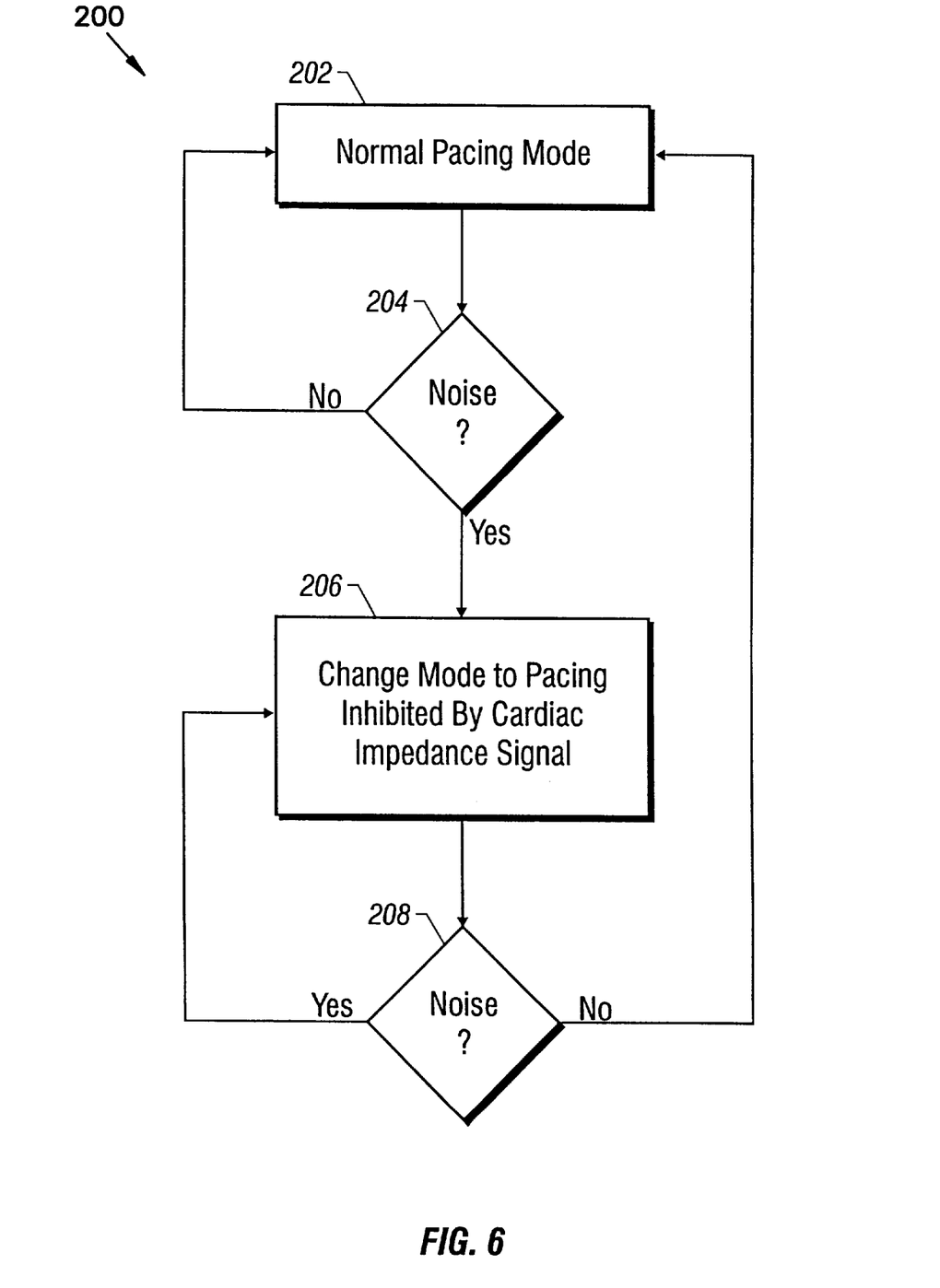
FIG. 6 is an exemplary operational flow diagram of the preferred embodiment of FIG. 5.

The operation of the ICD 100 is described generally with respect to the flow diagram 200 of FIG. 6. In step 202, the ICD 100 enters or remains in its normal, predetermined pacing mode suitable for the patient. Preferably, the normal pacing mode includes demand pacing based on the electrical activity of the heart at the electrodes. In step 204, if the ICD 100 is not in a high noise environment, the ICD 100 operationally remains in its normal pacing mode (step 202). However, if a high noise environment is detected in step 204, the processor 170 changes modes to the safe noise mode of the preferred embodiment (step 206). The preferred safe noise mode includes demand pacing that is inhibited in the vulnerable period which is determined from the heart's impedance or other cardiac-related parameters as described above. If it is determined that the heart is in the vulnerable period, processor 170 (FIG. 5) will not signal pulse generator 168 to provide a pacing pulse. In step 208, the processor 170 determines whether the ICD 100 is still in a high noise environment. If so, the ICD remains in the safe noise mode of operation to prevent the ICD from itself causing fibrillation. If not, the ICD 100 reverts back to its normal pacing mode of step 202.

Thus, the implantable device described above provides a significant improvement over the prior art. As explained, the invention permits demand-type pacing to continue during a large amplitude EMI event. Thus, the risk of pacing during the vulnerable period is much less than with prior art devices.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. A medical device adapted to be implanted in the human body for electrically stimulating the heart to beat and adapted to operate in at least two modes of operation, said medical device comprising:

a plurality of electrodes;

a sense circuit coupled to the electrodes;

a pulse generator coupled to the electrodes; and a heart status monitor including a processor, said heart status monitor coupled to at least two of said electrodes, and said heart status monitor generating a heart status signal indicative of the bio-mechanical state of the heart during a cardiac cycle;

said processor receiving the heart status signal and determining when the medical device is in a high noise environment and changing the mode of operation of the medical device to a safe noise mode in which the processor determines the bio-mechanical state of the heart by monitoring the heart status signal.

2. The medical device of claim 1 wherein said processor is coupled to said sense circuit and determines the bio-mechanical state of the heart by monitoring an output signal from the sense circuit.

3. The medical device of claim 2 wherein said processor discontinues monitoring the output signal from said sense circuit when the processor determines the medical device is in a high noise environment.

4. The medical device of claim 3 wherein said heart status monitor includes an impedance measurement circuit and said heart status signal is indicative of the impedance of the heart.

5. The medical device of claim 4 wherein said processor computes the impedance of the heart from the heart status signal.

6. The medical device of claim 5 wherein said cardiac cycle includes a vulnerable period of time and said processor determines said vulnerable period during said safe noise mode.

7. The medical device of claim 6 wherein said processor determines said vulnerable period from the impedance of the heart and inhibits pacing during said vulnerable period.

8. The medical device of claim 4 wherein the said heart status monitor includes a sensor that is adapted to respond to a cardiac parameter and that provides a sensor output signal to said processor that is indicative of said cardiac parameter.

9. The medical device of claim 8 wherein said cardiac cycle includes a vulnerable period of time and said processor determines said vulnerable period during said safe noise mode.

10. The medical device of claim 9 wherein said processor determines said vulnerable period from said sensor output signal during said safe noise mode and inhibits pacing during said vulnerable period.

11. The medical device of claim 10 wherein said sensor includes a pressure transducer.

12. The medical device of claim 10 wherein said sensor includes a flow transducer.

13. The medical device of claim 10 wherein said sensor includes a volume transducer.

14. The medical device of claim 10 wherein said sensor includes a cardiac sound transducer.

15. The medical device of claim 10 wherein said sensor includes an acceleration transducer.

16. An implantable medical device for electrically stimulating a human heart, including:

a plurality of electrodes;

a processor including a first mode and a second mode of operation;

an impedance circuit coupled to said processor, for generating a status signal indicative of the heart's impedance;

a pulse generator to stimulate the heart; and a sense circuit to process electrical signals from said electrodes;

said processor changes the operation of said medical device from said first mode to said second mode during a high noise event, and during said second mode said processor monitors the status signal, determines when a vulnerable period is occurring and inhibits pacing during said vulnerable period.

\* \* \* \* \*